(12) United States Patent
Cahoon et al.

(10) Patent No.: US 6,441,274 B1
(45) Date of Patent: Aug. 27, 2002

(54) PLANT TRYPTOPHAN SYNTHASE BETA SUBUNIT

(75) Inventors: Rebecca E. Cahoon, Wilmington; Saverio Carl Falco, Arden; Karin N. Lohman, Newark, all of DE (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/594,193

(22) Filed: Jun. 15, 2000

Related U.S. Application Data

(60) Provisional application No. 60/139,568, filed on Jun. 16, 1999.

(51) Int. Cl.[7] .......................... A01H 1/00; C07H 21/04; C07K 14/415; C12N 5/14; C12N 9/00
(52) U.S. Cl. .......................... 800/278; 435/6; 435/69.1; 435/71.1; 435/183; 435/410; 435/419; 435/252.3; 435/320.1; 530/350; 530/370; 536/23.1; 536/23.6; 536/24.1; 536/24.3; 536/24.33; 800/295
(58) Field of Search .................. 435/6, 69.1, 71.1, 435/183, 410, 419, 252.3, 320.1; 530/350, 370; 536/23.1, 23.6, 24.1, 24.3, 24.33; 800/278, 295

(56) References Cited

PUBLICATIONS

Sato et al. DNA Research, 1997, vol. 4, pp. 215–230.*
Elaine R. Radwanski et al., Mol. Gen. Genet., Arabidopsis thaliana tryptophan synthase alpha: gene cloning, expression, and subunit interaction, vol. 248:657–667, 1995.
Allen D. Wright et al., The Plant Cell, The Maize Auxotrophic Mutant orange pericarp is defective in duplicate genes for tryptophan synthase β, vol. 4:711–719, Jun. 1992.
National Center for Biotechnology Information General Identifier No. 2983814, Mar. 25, 1998.
Gerard Deckert et al., Nature, The complete genome of the hyperthermophilic bacterium Aquifex aeolicus, vol. 392:353–358, Mar. 26, 1998.
National Center for Biotechnology Information General Identifier No. 2649345, Dec. 15, 1997.
Hans–Peter Klenk et al., Nature, The complete genome sequence of the hyperthermophilic, sulphate–reducing archaeon Archaeoglobus fulgidus, vol. 390:364–370, Nov. 27, 1997.
National Center for Biotechnology Information General Identifier No. 7437017, Aug. 26, 1999.
National Center for Biotechnology Information General Identifier No. 168574, Apr. 27, 1993.
National Center for Biotechnology Information General Identifier No. 168572, Apr. 27, 1993.
Anthony L. Palombella et al., Plant Phys., vol. 117:455–464, 1998.

* cited by examiner

*Primary Examiner*—Phuong T. Bui

(57) ABSTRACT

This invention relates to an isolated nucleic acid fragment encoding a plant tryptophan synthase beta subunit. The invention also relates to the construction of a chimeric gene encoding all or a substantial portion of the plant tryptophan synthase beta subunit, in sense or antisense orientation, wherein expression of the chimeric gene results in production of altered levels of the plant tryptophan synthase beta subunit in a transformed host cell.

13 Claims, 5 Drawing Sheets

```
SEQ ID NO: 7    MRKFLLSEG------------------------------------------------
SEQ ID NO: 2    MAAAAATTLRTALSHSQATGQEQRASLLCTPEHRVAASRRSLRFTTRASSNAGAS---V
SEQ ID NO: 4    -HEVFPVNALPTPSPCFHSKVGKQWPQGFALSVR--PTNPKRLSSACKVRATLGASDKSI
SEQ ID NO:13    MA-----TALR---PPRLPAVPEQASSLHRLPKYRVAVTGRR-SFAARAGSYPG-N---V
                1                                                          60

*  !+*+*  ++*++**+*+++*  *    *  +*  *+ ++++*+++++
                                                                   ++  * ***
SEQ ID NO: 7    EIPKKWLNILPLLPEPLEPLPDPETMEPVKPEKLLAIFPEPLVEQEVSDKEWIDIPEEVL
SEQ ID NO: 2    SIPKQWYNLIADLPVKPPPPLHPQTHQPLNPSDLSPLFPDELIRQEVTDERFVDIPEEII
SEQ ID NO: 4    GIPNQWYNVIADLPVKPPPPLHPKTYEPIKPDDLSPLFPDELIRQEIASDRFIDIPDEVL
SEQ ID NO:13    GVPKQWYNLIADLPVKPPPMLHPGTHQPLNPSDLAPLFPDELIRQELTEERFIDIPDEVR
                61                                                        120

*+*  ***********+*******  +++++***  +++*++++++ +  ***+*++++
SEQ ID NO: 7    DIYSLWRPTPLHRAKNLEEFLGTPAKIFYKNESVSPPGSHKPNTAVAQAYYNKISGVKRL
SEQ ID NO: 2    DVYKLWRPTPLIRARRLEKLLGTPAKIYYKYEGTSPAGSHKPNTAVPQAWYNAAAGVKNV
SEQ ID NO: 4    DVYKLWRPTPLIRAKRLEKLLDTPARIYYKYEGVSPAGSHKPNSAVPQAWYNLQAGVKNV
SEQ ID NO:13    DVYELWRPTPLIRAKRLEKLLGTPAKIYYKYEGTSPAGSHKGNTAVPQAWYNAAAGVKNV
                121                                                       180

+  *  ********+****** +  **+****+++++*  **++*++**** *++*+
SEQ ID NO: 7    TTETGAGQWGSALSFATQFFDLQCRVYMVRVSYNQKPYRRILMETWKGEVIPSPSPYTNA
SEQ ID NO: 2    VTETGAGQWGSALSFASSLFGLNCEVWQVRASFDQKPYRRLMMETWGAKVHPSPSTATEA
SEQ ID NO: 4    VTETGAGQWGSALAFACSIFGLGCEVWQVRASYDSKPYRRLMMQTWGAKVHPSPSMITEA
SEQ ID NO:13    VTETGAGQWGSALSFASTLFGLNCEVWQVRASYDQKPYRRLMMETWGAKVHPSPSDVTEA
                181                                                       240
```

FIG. 1A

```
                  *     +   +*  +*****  ***** *******+*+*****  ********  +
SEQ ID NO: 7      GRKYYEENPEHPGSLGIAISEAIEEAASREDTKYSLGSVLNHVLLHQTVIGLEAKKQMEE
SEQ ID NO: 2      GKRILEADPSSPGSLGIAISEAVEVAATSADTKYCLGSVLNHVLLHQTVIGEECLEQLAA
SEQ ID NO: 4      GRRMLQEDPSSPGSPGSLGIAISEAVEVAAKNADTKYCLGSVLNHVLLHQSVIGEECIKQMEA
SEQ ID NO:13      GRKLLAADPASPGSLGMAISEAVEVAATNADTKYCLGSVLNHVLLHQTVIGEECLEQLAA
                  241                                                      300

*  +**  ***+*+******  **** **** ***  +++      +  +++++*+++ ******  +  ****  + *
SEQ ID NO: 7      AGYYPDVIIGAVGGGSNFAGLSFPFLADVLRGDKRKEDLKVLAVEPEACPTLTKGEYKYD
SEQ ID NO: 2      LGETPDVVIGCTGGGSNFGGLAFPFLREKLRG-RMSPAFR--AVEPAACPTLTKGVYAYD
SEQ ID NO: 4      IGETPDVIIGCTGGGSNFAGLSFPFLREKLNK-KINPVIR--AVEPAACPSLTKGVTYD
SEQ ID NO:13      IGDTPDVVIGCTGGGSNFGGLAFPFMREKLAG-RMSPQFK--AVEPAACPTLTKGVYAYD
                  301                                                          360

****+*  *****+++*******  ****  ***  *   +   **  +  **  ****+
SEQ ID NO: 7      FGDSVGLTPLIKMYTLGHDFVPSPIHAGGLRYHGDAPLVCKLYNLGYIDAVAYKQTEVFE
SEQ ID NO: 2      FGDTAGLTPLMKMHTLGHGFVPDPIHAGGLRYHGMAPLISHVYELGFMDAVAIQQTECFQ
SEQ ID NO: 4      YGDTAGMTPLMKMHTLGHDFVPDPIHAGGLRYHGMAPLISHVFDLGLMEAIAIPQTECFQ
SEQ ID NO:13      YGDTAGLTPLMKMHTLGHDFVPDPIHAGGLRYHGMAPLISHVYELGFMEAMSIQQTECFE
                  361                                                          420

****  **  *  ***++*******   *  *********+**  +++++++  **  *  **     ***
SEQ ID NO: 7      AAVTFARTEGIVPAPESAHAIKAAIDEALKCCKETGEEKVILFNLSGHGYFDLSAYDKYLH
SEQ ID NO: 2      AALQFARTEGIIPAPEPTHAIAAAIREALECKRTGEEKVILMAMCGHGHFDLAAYEKYLR
SEQ ID NO: 4      GAIQFARSEGLIPAPEPTHAIAATIREAIRCREAGEAKVILTAMCGHGHFDLPAYEKYLQ
SEQ ID NO:13      AALQFARTEGIIPAPEPTHAIAAAIREALECKRTGEEKVILIAMCGHGHFDLAAYDRYLR
                  421                                                          480
```

FIG. 1B

```
                  *  +  *++      +       ++      +  +
SEQ ID NO: 7      GELTD----------------------------   
SEQ ID NO: 2      GDMVDLSHPAEKLEASLAAVPKV--
SEQ ID NO: 4      GNMVDLSFSEDKMKASLANIPQVIT
SEQ ID NO:13      GDMIDLSHSSEKLKESLGAIPKV--
                  481                            505
```

FIG. 1C

```
SEQ ID NO:8    ------------------------------------------------------------
SEQ ID NO:9    PGPPPPAPEGRRRGRGRNAAGQAVAAEASPAAVEMGNG----------AAAPGLQRPDA
SEQ ID NO:2    MAAAAAATTLRTALSHSQATGQEQRASLLCTPEHRVAASRRSLRFTTRASSNAGASVSIP
                                                                            60
               1

++++++++ *+++++++*++ +*+++ +*++++++++*++++++*++++
SEQ ID NO:8    -----GRFGGKYV-PETLMHALT-------ELENAF------HALATDDEFQKELDGILKDY
SEQ ID NO:9    MGRFGRFGGKYV-PETLMHALT-------ELESAF------HALATDDEFQKELDGILKDY
SEQ ID NO:2    KQWYNLIADLPVKPPPPLHPQTHQPLNPSDLSPLFPDELIRQEVTDERFVDIPEEIIDVY
                                                                            120
               61

++++++*++++++++*+++++++++ *++*++*+++++++ *+*+*+++*+++++++
SEQ ID NO:8    -VGRESPLYFAERLTEHYKRADGTGPLIYLKREDLNHRGAHKINNAVAQALLAKRLGKQR
SEQ ID NO:9    -VGRESPLYFAERLTEHYKRADGTGPLIYLKREDLNHTGAHKINNAVAQALLAKRLGKQR
SEQ ID NO:2    KLWRPTPLIRARRLE----KLLGTPAKIYYKYEGTSPAGSHKPNTAVPQAWYNAAAGVKN
                                                                            180
               121

+++++++++++++++++++++ +*+++*++*+*++*++++*+*+ ++ +*+++++++
SEQ ID NO:8    IIAETGAGQHGVATATVCARFGLQCIIYMGAQDMERQALNVFRMKLLGAEVRAVHSGTA-
SEQ ID NO:9    IIAETGAGQHGVATATVCRRFGLQCIIYMGAQDMERQALNVFRMRLLGAEVRAVHSGTA-
SEQ ID NO:2    VVTETGAGQWGSALSFASSLFGLNCEVWQVRASFDQKPYRRLMMETWGAKVHPSPSTATE
                                                                            240
               181

+++++++++++++++ ++++++++++++++*++++*+++*+*+++++++*+*****+
SEQ ID NO:8    ----------------TLKDATSEAIRDWTNVETTHYILGSVAGPHPYPMMVREFHKVIGK
SEQ ID NO:9    ----------------TLKDATSEAIRDWTNVETTHYILGSVAGPHPYPMMVREFHKVIGK
SEQ ID NO:2    AGKRILEADPSSPGSLGIAISEAVEVAATSADTK-YCLGSVLN----HVLLH--QTVIGE
                                                                            300
               241
```

FIG. 2A

```
                *+++++++ +++++++*+*+++++ +* +++++++++*+++++++ +  * +++++++++++++++
SEQ ID NO:8     ETRRQAMHKWGGKPDVLVACVGGGSNAMGLFHEFVEDQDVRLIGVEAAGHGVDTDKHAAT
SEQ ID NO:9     ETRRQAMDKWGGKPDVLVACVGGGSNAMGLFHEFVEDQDVRLVGLEAAGHGVDTDKHAAT
SEQ ID NO:2     ECLEQ-LAALGETPDVVIGCTGGGSNFGGLAFPFLRE---KLRGRMSPAFRAVEPAACPT
                                                                          360

*++++*+++++*++++*++++++++++++++ ++*+*+++++++++*+*+++++++*++++
SEQ ID NO:8     LTKG----QVGVLHGSMSYLLQDDDGQVIEPHSI-SAGLDYPGVGPEHSFLKDIGRAEYD
SEQ ID NO:9     LTKG----QVGVLHGSMSYLLQDDDGQVIEPHSI-SAGLDYPGVGPEHSFLKDIGRAEYD
SEQ ID NO:2     LTKGVYAYDFGDTAGLTPLMKMHTLGHGFVPDPIHAGGLRYHGMAPLISHVYELGFMDAV
                                                                          420

+++++*+++++*+++++*+++++++++++++++++ +++++ ++++++ +++++*+++++
SEQ ID NO:8     SVTDQEALDAFKRVSRLEGIIPALETSHALA--YLEKL-CPTLPDGVRVVLNCSGRGDKD
SEQ ID NO:9     SVTDQEALDAFKRVSRLEGIIPALETSHALA--YLEKL-CPTLADGVRVVVNCSGRGDKD
SEQ ID NO:2     AIQQTECFQAALQFARTEGIIPAPEPTHAIAAAIREALECKRTGEEKVILMAMCGHGHED
                                                                          480

+++++*++++*++++++++++++++++++++++*
SEQ ID NO:8     VHTASKYLD-------------------V
SEQ ID NO:9     VHTASKYLD-------------------V
SEQ ID NO:2     LAAYEKYLRGDMVDLSHPAEKLEASLAAVPKV
                                                513
```

FIG. 2B

PLANT TRYPTOPHAN SYNTHASE BETA SUBUNIT

This application claims priority benefit of U.S. Provisional Application No. 60/139,568 filed Jun. 16, 1999, now pending.

FIELD OF THE INVENTION

This invention is in the field of plant molecular biology. More specifically, this invention pertains to nucleic acid fragments encoding a novel tryptophan synthase beta subunit in plants and seeds.

BACKGROUND OF THE INVENTION

Many vertebrates, including man, lack the ability to manufacture a number of amino acids and therefore require these amino acids preformed in their diet. These are called essential amino acids. Plants are able to synthesize all twenty amino acids and serve as the ultimate source of the essential amino acids for humans and animals. Thus, the ability to manipulate the production and accumulation of the essential amino acids in plants is of considerable importance and value. Furthermore, the inability of animals to synthesize these amino acids provides a useful distinction between animal and plant cellular metabolism. This can be exploited for the discovery of herbicidal chemical compounds that target enzymes in the plant biosynthetic pathways of the essential amino acids and have low toxicity to animals.

In plants the tryptophan pathway leads to the biosynthesis of many secondary metabolites including the hormone indole-3-acetic acid, antimicrobial phytoalexins, alkaloids and glucosinolates. The two final reactions in tryptophan biosynthesis are catalyzed by tryptophan synthase. The 29 kDa alpha subunit is a bifunctional enzyme which cleaves indole-3-glycerol phosphate to produce indole and glyceraldehyde-3-phosphate. The beta subunit joins indole with serine to form tryptophan. Either subunit alone is enzymatically active, but the rate of the reaction and affinity for the substrates increases when the subunits are forming a tetramer composed of two alpha subunits and two beta subunits (Radwanski (1995) *Mol. Gen. Genet.* 248:657–667).

Few of the genes encoding enzymes from the tryptophan pathway in corn, soybeans, rice and wheat have been isolated and sequenced. Corn genes encoding tryptophan synthase beta subunits have been identified (Wright et al. (1992) *Plant Cell* 4:711–719). The instant invention describes novel corn, rice, soybean, and wheat tryptophan synthase beta subunit homologs.

SUMMARY OF THE INVENTION

The present invention concerns an isolated polynucleotide comprising a nucleotide sequence selected from the group consisting of: (a) a first nucleotide sequence comprising a polynucleotide of at least 700 nucleotides from SEQ ID NO:1; (b) a second nucleotide sequence comprising a polynucleotide sequence of at least 420 nucleotides from the group consisting of SEQ ID NOs:3, 5, 10, and 12; (c) a third nucleotide sequence encoding a polypeptide of at least 100 amino acids having at least 80% identity based on the Clustal method of alignment when compared to a polypeptide selected from the group consisting of SEQ ID NOs:2, 4, 6, 11, and 13; and (d) a fourth nucleotide sequence comprising a complement of the first or second nucleotide sequences.

In a second embodiment, this invention concerns an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 10, and 12 and the complement of such nucleotide sequences.

In a third embodiment, this invention relates to a chimeric gene comprising an isolated polynucleotide of the present invention operably linked to at least one suitable regulatory sequence.

In a fourth embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a fifth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a sixth embodiment, the invention concerns a novel plant tryptophan synthase beta subunit polypeptide of at least 100 amino acids comprising at least 80% identity based on the Clustal method of alignment when compared to a polypeptide selected from the group consisting of SEQ ID NOs:2, 4, 6, 11, and 13.

In an seventh embodiment, the invention relates to a method of selecting an isolated polynucleotide that affects the level of expression of a novel plant tryptophan synthase beta subunit polypeptide or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the novel plant tryptophan synthase beta subunit polypeptide or enzyme activity in the host cell containing the isolated polynucleotide; and (d) comparing the level of the novel plant tryptophan synthase beta subunit polypeptide or enzyme activity in the host cell containing the isolated polynucleotide with the level of the novel plant tryptophan synthase beta subunit polypeptide or enzyme activity in the host cell that does not contain the isolated polynucleotide.

In a eighth embodiment, the invention concerns a method of obtaining a nucleic acid fragment encoding a substantial portion of a novel plant tryptophan synthase beta subunit polypeptide, preferably a plant novel plant tryptophan synthase beta subunit polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 10, and 12 and the complement of such nucleotide sequences; and amplifying a nucleic acid fragment (preferably a cDNA inserted in a cloning vector) using the oligonucleotide primer. The amplified nucleic acid fragment preferably will encode a substantial portion of a novel plant tryptophan synthase beta subunit amino acid sequence.

In a ninth embodiment, this invention relates to a method of obtaining a nucleic acid fragment encoding all or a substantial portion of the amino acid sequence encoding a novel plant tryptophan synthase beta subunit polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a tenth embodiment, this invention concerns a composition, such as a hybridization mixture, comprising an isolated polynucleotide or an isolated polypeptide of the present invention.

In an eleventh embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the novel plant tryptophan synthase beta subunit polynucleotide in an amount sufficient to complement a null mutant to provide a positive selection means.

In a twelfth embodiment, this invention relates to a method of altering the level of expression of a novel plant tryptophan synthase beta subunit in a host cell comprising: (a) transforming a host cell with a chimeric gene of the present invention; and (b) growing the transformed host cell under conditions that are suitable for expression of the chimeric gene wherein expression of the chimeric gene results in production of altered levels of the novel plant tryptophan synthase beta subunit in the transformed host cell.

A further embodiment of the instant invention is a method for evaluating at least one compound for its ability to inhibit the activity of a novel plant tryptophan synthase beta subunit, the method comprising the steps of: (a) transforming a host cell with a chimeric gene comprising a nucleic acid fragment encoding a novel plant tryptophan synthase beta subunit polypeptide, operably linked to at least one suitable regulatory sequence; (b) growing the transformed host cell under conditions that are suitable for expression of the chimeric gene wherein expression of the chimeric gene results in production of the tryptophan synthase beta subunit in the transformed host cell; (c) optionally purifying the novel plant tryptophan synthase beta subunit polypeptide expressed by the transformed host cell; (d) treating the novel plant tryptophan synthase beta subunit polypeptide with a compound to be tested; and (e) comparing the activity of the novel plant tryptophan synthase beta subunit polypeptide that has been treated with a test compound to the activity of an untreated novel plant tryptophan synthase beta subunit polypeptide, thereby selecting compounds with potential for inhibitory activity.

BRIEF DESCRIPTION OF THE DRAWINGS AND SEQUENCE LISTINGS

The invention can be more fully understood from the following detailed description, the accompanying drawings and Sequence Listing which form a part of this application.

FIG. 1 depicts the amino acid sequence alignment between the tryptophan synthase beta subunit from *Aquifex aeolicus* (NCBI General Identifier No. 293814; SEQ ID NO:7), the instant corn clone ccase-b.pk0015.e7 (SEQ ID NO:2), the instant soybean clone sfl1.pk131.b23 (SEQ ID NO:4), and the instant wheat clone wdk2c.pk005.o10:fis (SEQ ID NO:13). Amino acids which are identical among all sequences are indicated with an asterisk (*) above the alignment while those conserved only among the plant sequences are indicated by a plus sign (+) above the alignment. Dashes are used by the program to maximize alignment of the sequences.

FIG. 2 depicts the amino acid sequence alignment between the tryptophan synthase beta subunits from corn having NCBI General Identifier No. 168572 (SEQ ID NO:8) and NCBI General Identifier No. 168574 (SEQ ID NO:9) and the instant corn clone ccase-b.pk0015.e7 (SEQ ID NO:2). Amino acids which are identical among all sequences are indicated with an asterisk (*) above the alignment while those conserved only among the sequences in the public domain are indicated by a plus sign (+) above the alignment. Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Novel Plant Tryptophan Synthase Beta Subunit

| | | SEQ ID NO: | |
|---|---|---|---|
| Protein | Clone Designation | (Nucleotide) | (Amino Acid) |
| Corn Tryptophan Synthase Beta Subunit | ccase-b.pk0015.e7 | 1 | 2 |
| Soybean Tryptophan Synthase Beta Subunit | sfl1.pk131.b23 | 3 | 4 |
| Wheat Tryptophan Synthase Beta Subunit | wdk2c.pk005.o10 | 5 | 6 |
| Rice Tryptophan Synthase Beta Subunit | Contig of: rdr1f.pk003.m17 rlr12.pk0007.g7 | 10 | 11 |
| Wheat Tryptophan Synthase Beta Subunit | wdk2c.pk005.o10:fis | 12 | 13 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from SEQ ID NOs:1, 3, 5, 10, and 12, or the complement of such sequences.

The term "isolated polynucleotide" refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 10, and 12, and the complement of such nucleotide sequences may be used in methods of selecting an isolated polynucleotide that affects the expression of a novel plant tryptophan synthase beta subunit polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS which was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed MRNA upstream of the translation start sequence. The translation leader sequence may affect processing of the primary transcript to MRNA, MRNA stability or translation efficiency. Examples of translation leader sequences have been described (Turner and Foster (1995) *Mol. Biotechnol.* 3:225–236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the MRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an MRNA template. The cDNA can be single-stranded or converted to double stranded form using, for example, the Klenow fragment of DNA polymerase I. "Sense RNA" refers to an RNA transcript that includes the MRNA and can be translated into a polypeptide by the cell. "Antisense RNA" refers to an RNA transcript that is complementary to all or part of a target primary transcript or MRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence.

"Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to translation of MRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refer to the production of gene product(s) in tansgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al., *Molecular Cloning: A Laboratory Manual;* Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence comprising a polynucleotide of at least 700 nucleotides from SEQ ID NO:1; (b) a second nucleotide sequence comprising a polynucleotide of at least 420 nucleotides from the group consisting of SEQ ID NOs:3, 5, 10, and 12; (c) a third nucleotide sequence encoding a polypeptide of at least 100 amino acids having at least 80% identity based on the Clustal method of alignment when compared to a polypeptide selected from the group consisting of SEQ ID NOs:2, 4, 6, 11, and 13; and (d) a fourth nucleotide sequence comprising the complement of the first or second nucleotide sequences.

Nucleic acid fragments encoding at least a substantial portion of several novel plant tryptophan synthase beta subunits have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other novel plant tryptophan synthase beta subunits, either as cDNAs or genomic DNAs, could be isolated directly by using all or a substantial portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 10, and 12 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a novel plant tryptophan synthase beta subunit polypeptide, preferably a substantial portion of a plant novel plant tryptophan synthase beta subunit polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 10, and 12, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a novel plant tryptophan synthase beta subunit polypeptide.

Availability of the instant nucleotide and deduced amino acid sequences facilitates immunological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of tryptophan in those cells. The tryptophan synthase beta subunit sequences included in this application are similar to bacterial tryptophan synthase beta subunit genes but distantly related to the previously known plant tryptophan synthase beta subunit genes. Inactivation by mutation of the two previously known corn tryptophan synthase beta subunit genes causes corn to require tryptophan for growth. Inactivation by mutation of one of the previously known Arabidopsis tryptophan synthase beta subunit genes causes tryptophan auxotrophy suggesting the presence of other tryptophan synthase beta subunits in plants. Inhibition of this enzyme may lead to cell death because the substrate of the enzyme, indole, is toxic. Manipulation of the levels of this tryptophan synthase beta subunit may lead to the production of higher levels of tryptophan.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) with or without removing targeting sequences that are already present. While the references cited give examples of each of these, the list is not exhaustive and more targeting signals of use may be discovered in the future.

In another embodiment, the present invention concerns a polypeptide of at least 100 amino acids that has at least 80% identity based on the Clustal method of alignment when compared to a polypeptide selected from the group consisting of SEQ ID NOs:2, 4, 6, 11, and 13.

The instant polypeptides (or substantial portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded novel plant tryptophan synthase beta subunit. An example of a vector for high level expression of the instant polypeptides in a bacterial host is provided (Example 6).

Additionally, the instant polypeptides can be used as targets to facilitate design and/or identification of inhibitors of those enzymes that may be useful as herbicides. This is desirable because the tryptophan synthase beta subunit described herein catalyzes the last step in tryptophan synthesis from chorismic acid. Accordingly, inhibition of the activity of the enzyme described herein could lead to inhibition plant growth. Thus, the instant tryptophan synthase beta subunit could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---------|--------|-------|
| ccase-b | Corn Callus Type II Tissue, Somatic Embryo Formed, Highly Transformable | ccase-b.pk0015.e7 |
| sfl1 | Soybean Immature Flower | sfl1.pk131.b23 |
| rlr12 | Rice Leaf 15 Days After Germination, 12 Hours After Infection of Strain *Magaporthe grisea* 4360-R-62 (AVR2-YAMO); Resistant | rlr12.pk0007.g7 |
| rdr1f | Rice Developing Root of 10 Day Old Plant | rdr1f.pk003.m17 |
| wdk2c | Wheat Developing Kernel, 7 Days After Anthesis | wdk2c.pk005.o10 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, CA). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding novel plant tryptophan synthase beta subunits were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of CDNA Clones Encoding Novel Tryptophan Synthase Beta Subunits The BLASTX search using the EST sequences from clones listed in Table 3 revealed similarity of the polypeptides encoded by the cDNAs to tryptophan synthase beta subunit from *Aquifex aeolicus* (NCBI General Identifier No. 2983814) or *Archaeoglobus fulgidus* (NCBI General Identifier No. 2649345). Shown in Table 3 are the BLAST results for individual ESTs ("EST"), or for the sequences of the entire cDNA inserts comprising the indicated cDNA clones encoding the entire protein ("CGS"):

TABLE 3

BLAST Results for Sequences Encoding Polypeptides Homologous to Tryptophan Synthase Beta Subunit

| Clone | Status | Organism | BLAST pLog Score NCBI GI No. | BLAST pLog Score |
|---|---|---|---|---|
| ccase-b.pk0015.e7 | CGS | Aquifex aeolicus | 2983814 | >254 |
| sfl1.pk131.b23 | CGS | Aquifex aeolicus | 2983814 | 180.0 |
| wdk2c.pk005.o10 | EST | Archaeoglobus fulgidus | 2649345 | 8.22 |

The sequence of the entire cDNA insert in clone wdk2c.pk005.o10 was determined and further sequencing and searching of the Du Pont proprietary EST Database allowed the identification of rice ESTs encoding tryptophan synthase beta subunit homologs. The BLASTX search using the EST sequences from clones listed in Table 4 revealed similarity of the polypeptides encoded by the cDNAs to tryptophan synthase beta subunit from *Aquifex aeolicus* (NCBI General Identifier No. 7437010) or *Archaeoglobus fulgidus* (NCBI General Identifier No. 7437017) The amino acid sequence having NCBI General Identifier No. 7437010 is 100% identical to the amino acid sequence having NCBI General Identifier No. 2983814 and the amino acid sequence having NCBI General Identifier No. 7437017 is 100% identical to the amino acid sequence having NCBI General Identifier No. 2649345. Shown in Table 4 are the BLAST results for the sequences of contigs assembled from two or more ESTs ("Contig") or the sequences of the entire cDNA inserts comprising the indicated cDNA clones encoding an entire protein ("CGS"):

TABLE 4

BLAST Results for Sequences Encoding Polypeptides Homologous to Tryptophan Synthase Beta Subunit

| Clone | Status | Organism | NCBI GI No. | BLAST pLog Score |
|---|---|---|---|---|
| Contig of: rdr1f.pk003.m17 rlr12.pk0007.g7 | Contig | Archaeoglobus fulgidus | 7437017 | 28.70 |
| wdk2c.pk005.o10:fis | CGS | Aquifex aeolicus | 7437010 | 156.00 |

FIG. 1 presents an alignment of the amino acid sequences set forth in SEQ ID NOs:2, 4, and 13 and the *Aquifex aeolicus* sequence (NCBI General Identifier No. 29831814, SEQ ID NO:7). The data in Table 5 presents a calculation of the percent identity of the amino acid sequences set forth in SEQ ID NOs:2, 4, 6, 11, and 13 and the *Aquifex aeolicus* sequence (SEQ ID NO:7).

TABLE 5

Percent Identity of Amino Acid Sequences Deduced From the Nucleotide Sequences of cDNA Clones Encoding Polypeptides Homologous to Tryptophan Synthase Beta Subunit

| SEQ ID NO. | Percent Identity to 29831814 |
|---|---|
| 2 | 61.3 |
| 4 | 59.2 |
| 6 | 17.7 |

TABLE 5-continued

Percent Identity of Amino Acid Sequences Deduced From the Nucleotide Sequences of cDNA Clones Encoding Polypeptides Homologous to Tryptophan Synthase Beta Subunit

| SEQ ID NO. | Percent Identity to 29831814 |
|---|---|
| 11 | 32.6 |
| 13 | 59.9 |

The corn amino acid sequence is 71.8% identical to the soybean sequence and 82.8% identical to the wheat sequence encoding an entire tryptophan synthase beta synthase while the soybean sequence is 72.1% identical to the wheat sequence.

There are amino acid sequences for two corn tryptophan synthase beta subunits in the NCBI database. The sequence having General Identifier No. 168572 lacks 54 N-terminal amino acids present in the sequence having General Identifier No. 168574 and there are 9 differences in the rest of the amino acid sequence making these sequences 97.7% identical to each other. FIG. 2 presents an alignment of the amino acid sequences set forth in SEQ ID NO:2 and the corn tryptophan synthase beta subunits present in the NCBI database (General Identifier No. 168572, SEQ ID NO:8, and General Identifier No. 168574, SEQ ID NO:9). The sequence from clone ccase-b.pk0015.e7 (SEQ ID NO:2) is 22.1% identical to SEQ ID NO:8 and 21.0% identical to SEQ ID NO:9.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode entire or nearly entire corn, soybean, and wheat novel tryptophan synthase beta subunits and a substantial portion of a wheat and a rice novel tryptophan synthase beta subunits.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C.overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of mercury (Hg). The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches of mercury (Hg). The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C.for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Novel Plant Tryptophan Synthase Beta Subunits The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. Assays for tryptophan synthase beta subunit are presented by Palombella and Dutcher (1998) *Plant Physiol.* 117:455–464.

What is claimed is:

1. An isolated polynucleotide comprising:
   (a) a nucleotide sequence encoding a polypeptide having tryptophan synthase beta subunit activity, wherein the amino acid sequence of the polypeptide and the amino acid sequence of SEQ ID NO:2 have at least 80% sequence identity based on the Clustal alignment method, or
   (b) the complement of the nucleotide sequence, wherein the complement and the nucleotide sequence contain the same number of nucleotides and are 100% complementary.

2. The polynucleotide of claim 1 wherein the amino acid sequence of the polypeptide and the amino acid sequence of SEQ ID NO:2 have at least 85% sequence identity based on the Clustal alignment method.

3. The polynucleotide of claim 1 wherein the amino acid sequence of the polypeptide and the amino acid sequence of SEQ ID NO:2 have at least 90% sequence identity based on the Clustal alignment method.

4. The polynucleotide of claim 1 wherein the amino acid sequence of the polypeptide and the amino acid sequence of SEQ ID NO:2 have at least 95% sequence identity based on the Clustal alignment method.

5. The polynucleotide of claim 1 wherein the polypeptide comprises the amino acid sequence of SEQ ID NO:2.

6. The polynucleotide of claim 1 wherein the nucleotide sequence comprises the nucleotide sequence of SEQ ID NO:1.

7. A vector comprising the polynucleotide of claim 1.

8. A recombinant DNA construct comprising the polynucleotide of claim 1 operably linked to a regulatory sequence.

9. A method for transforming a cell comprising transforming a cell with the polynucleotide of claim 1.

10. A cell comprising the recombinant DNA construct of claim 8.

11. A method for producing a plant comprising transforming a plant cell with the polynucleotide of claim 1 and regenerating a plant from the transformed plant cell.

12. A plant comprising the recombinant DNA construct of claim 8.

13. A seed comprising the recombinant DNA construct of claim 8.

* * * * *

SEQUENCE LISTING

```
<160> NUMBER OF SEQ ID NOS:  13

<210> SEQ ID NO 1
<211> LENGTH: 1739
<212> TYPE: DNA
<213> ORGANISM: Zea mays

<400> SEQUENCE: 1
gcacgaggga aggcagtcac ttctccagga gcccggagtc ggcagcgaga gagaatggcc    60
```

```
gccgccgccg ccgccaccac ccttcgtact gctctctccc actcccaagc aacagggcaa      120
gagcagagag cttcactgct ttgcacaccg gagcaccgag ttgctgccag caggagaagc      180
ttgagattca ccactagggc cagctcgaat gcgggcgcca gtgtgagcat cccgaagcaa      240
tggtacaacc tcatcgccga cctgccggtg aagccaccgc caccgctgca cccgcagaca      300
caccagcctc tgaatcccag cgacctctcc cctctgttcc ccgacgagct gatcaggcag      360
gaggtcaccg acgagcggtt cgtcgacata cccgaggaga tcatcgacgt gtacaagctc      420
tggcgcccga cgcccctgat cagggccagg aggctggaga gctgctcgg cacgccggcc       480 aagatctact acaagtacga ggggaccagc ccggcggggt cgcacaagcc aacaccgcc       540 gtgccgcagg cgtggtacaa cgccgcggcg ggggtgaaga acgtggtcac cgagaccggc      600
gccggccagt ggggcagcgc gctgtccttc gccagcagcc tcttcggcct taactgcgag      660
gtatggcagg tgcgcgcgtc gttcgaccag aagccgtacc ggaggctgat gatgagacg       720 tggggcgcca aggtgcaccc gtcgccgtcg acggcgacgg aggccggcaa gaggatcctg      780
gaggcggacc cgtccagccc gggcagcctc gggatcgcca tctccgaggc ggtggaggtg      840
gcggccacca gcgccgacac caagtactgc ctgggcagcg tgctcaacca cgtcctgctc      900
caccagaccg tcatcgggga ggagtgcctg gagcagctag cggcgctcgg cgagacgccc      960
gacgtcgtca tcggctgcac cggcggcggg tccaacttcg gcgggctcgc gttcccgttc     1020
ttgcgcgaga agctgcgcgg caggatgagc ccgcgttca gggccgtgga gcccgccgcg      1080
tgccccacgc tcaccaaggg cgtctacgcg tacgacttcg gcgacacggc cgggctcacg     1140
ccgctgatga agatgcacac cctcggccac ggcttcgtcc ccgacccgat ccatgcaggt     1200
gggcttcggt accatggaat ggcacctctg atctcgcacg tgtacgagct gggcttcatg     1260
gatgccgttg ctatacagca gactgaatgc ttccaagctg ccttgcaatt cgccaggacg     1320
gagggcatca tcccggcgcc ggagccgacg cacgcaatcg ccgcggcgat cagggaggcg     1380
ctggagtgca gcggaccgg ggaggagaag gtcatcctga tggccatgtg cgggcacgga      1440
catttcgacc tcgccgcgta cgagaagtac ctgagggag acatggtcga tctctcgcac     1500
ccggcggaga gctggaggc ctccctcgct gccgtgccca agtctgacg gcgttggagc       1560 caactgcaca tgcgactgga atgggacgaa taatccattg atatcaggtt cttgaatctt     1620
gtggtgatcc atcgcccatc ggcagtggga tacttgtgtt ccttatgaaa tgaatgaata     1680
aaatttcaat aaaagcattt attttatcaa aaaaaaaaaa aaaaaaaaaa aaaaaaaa      1739
```

<210> SEQ ID NO 2
<211> LENGTH: 497
<212> TYPE: PRT
<213> ORGANISM: Zea mays

<400> SEQUENCE: 2

```
Met Ala Ala Ala Ala Ala Thr Thr Leu Arg Thr Ala Leu Ser His
 1               5                  10                  15

Ser Gln Ala Thr Gly Gln Glu Gln Arg Ala Ser Leu Leu Cys Thr Pro
            20                  25                  30

Glu His Arg Val Ala Ala Ser Arg Arg Ser Leu Arg Phe Thr Thr Arg
        35                  40                  45

Ala Ser Ser Asn Ala Gly Ala Ser Val Ser Ile Pro Lys Gln Trp Tyr
    50                  55                  60

Asn Leu Ile Ala Asp Leu Pro Val Lys Pro Pro Pro Leu His Pro
 65                 70                  75                  80
```

-continued

Gln Thr His Gln Pro Leu Asn Pro Ser Asp Leu Ser Pro Leu Phe Pro
                85                  90                  95

Asp Glu Leu Ile Arg Gln Glu Val Thr Asp Glu Arg Phe Val Asp Ile
            100                 105                 110

Pro Glu Glu Ile Ile Asp Val Tyr Lys Leu Trp Arg Pro Thr Pro Leu
            115                 120                 125

Ile Arg Ala Arg Arg Leu Glu Lys Leu Leu Gly Thr Pro Ala Lys Ile
    130                 135                 140

Tyr Tyr Lys Tyr Glu Gly Thr Ser Pro Ala Gly Ser His Lys Pro Asn
145                 150                 155                 160

Thr Ala Val Pro Gln Ala Trp Tyr Asn Ala Ala Gly Val Lys Asn
                165                 170                 175

Val Val Thr Glu Thr Gly Ala Gly Gln Trp Gly Ser Ala Leu Ser Phe
                180                 185                 190

Ala Ser Ser Leu Phe Gly Leu Asn Cys Glu Val Trp Gln Val Arg Ala
            195                 200                 205

Ser Phe Asp Gln Lys Pro Tyr Arg Arg Leu Met Met Glu Thr Trp Gly
    210                 215                 220

Ala Lys Val His Pro Ser Pro Ser Thr Ala Thr Glu Ala Gly Lys Arg
225                 230                 235                 240

Ile Leu Glu Ala Asp Pro Ser Ser Pro Gly Ser Leu Gly Ile Ala Ile
                245                 250                 255

Ser Glu Ala Val Glu Val Ala Ala Thr Ser Ala Asp Thr Lys Tyr Cys
            260                 265                 270

Leu Gly Ser Val Leu Asn His Val Leu Leu His Gln Thr Val Ile Gly
    275                 280                 285

Glu Glu Cys Leu Glu Gln Leu Ala Ala Leu Gly Glu Thr Pro Asp Val
290                 295                 300

Val Ile Gly Cys Thr Gly Gly Gly Ser Asn Phe Gly Gly Leu Ala Phe
305                 310                 315                 320

Pro Phe Leu Arg Glu Lys Leu Arg Gly Arg Met Ser Pro Ala Phe Arg
                325                 330                 335

Ala Val Glu Pro Ala Ala Cys Pro Thr Leu Thr Lys Gly Val Tyr Ala
            340                 345                 350

Tyr Asp Phe Gly Asp Thr Ala Gly Leu Thr Pro Leu Met Lys Met His
    355                 360                 365

Thr Leu Gly His Gly Phe Val Pro Asp Pro Ile His Ala Gly Gly Leu
    370                 375                 380

Arg Tyr His Gly Met Ala Pro Leu Ile Ser His Val Tyr Glu Leu Gly
385                 390                 395                 400

Phe Met Asp Ala Val Ala Ile Gln Gln Thr Glu Cys Phe Gln Ala Ala
                405                 410                 415

Leu Gln Phe Ala Arg Thr Glu Gly Ile Ile Pro Ala Pro Glu Pro Thr
            420                 425                 430

His Ala Ile Ala Ala Ile Arg Glu Ala Leu Glu Cys Lys Arg Thr
            435                 440                 445

Gly Glu Glu Lys Val Ile Leu Met Ala Met Cys Gly His Gly His Phe
    450                 455                 460

Asp Leu Ala Ala Tyr Glu Lys Tyr Leu Arg Gly Asp Met Val Asp Leu
465                 470                 475                 480

Ser His Pro Ala Glu Lys Leu Glu Ala Ser Leu Ala Ala Val Pro Lys
                485                 490                 495

Val

<210> SEQ ID NO 3
<211> LENGTH: 1817
<212> TYPE: DNA
<213> ORGANISM: Glycine max
<220> FEATURE:
<221> NAME/KEY: unsure
<222> LOCATION: (1809)..(1810)..(1811)..(1812)
<221> NAME/KEY: unsure
<222> LOCATION: (1814)

<400> SEQUENCE: 3

```
gcacgaggtt ttccctgtta atgcacttcc tactccttca ccatgtttcc actccaaagt      60
tggaaagcaa tggcctcagg gatttgcctt gagtgtgagg ccaacgaatc cgaagaggct     120
ttcaagtgcc tgcaaagtga gagcaacttt gggtgcttct gataaatcaa ttggaattcc     180
caaccaatgg tacaatgtaa ttgcagatct tccagtgaaa ccacctccac cattgcatcc     240
caagacttat gaaccaatca accagatga  cttgtcaccc cttttcctg  atgagttaat     300
cagacaagag atcgccagtg acagattcat agacatacca gatgaagttc ttgatgttta     360
caagctttgg cgcccgaccc ctctcattag agccaagagg ctggaaaagc ttcttgatac     420
gccggctaga atttactaca agtatgaagg tgtaagcccc gctggatcac acaaaccaaa     480
ctctgctgtt ccacaagcct ggtataattt acaagcaggt gtcaagaatg ttgtgacaga     540
aactggtgct ggacagtggg gaagtgcatt ggcctttgcg tgcagcatat ttggtcttgg     600
ctgtgaggtg tggcaagtac gtgcttctta tgattcaaaa ccatatcgga gattgatgat     660
gcaaacatgg ggtgcaaagg tacacccatc tccatctatg attactgagg caggtcggag     720
aatgcttcaa gaggatccat caagcccagg gagtttaggc atagccatat cagaagctgt     780
ggaggttgct gctaaaaatg ctgataccaa gtactgcttg gggagtgtac tcaatcatgt     840
tttactccac cagagtgtta taggagaaga gtgcatcaaa caaatggaag ctattgggga     900
aaccccagat gtcattatag gatgtactgg tggtggctcc aactttgcag gacttagttt     960
cccgttcctt cgagagaagc tcaataaaaa aatcaatcct gttataagag cggttgaacc    1020
tgcagcatgt ccttcattaa caaaagggt  atatacttat gattatggtg atacagcagg    1080
gatgactcca ttgatgaaaa tgcacacact tggacacgac tttgttccgg atccaattca    1140
tgctggggt  ttgcgttacc acggtatggc accattgatc tcacatgttt tgacttggg    1200
tttaatggaa gcaattgcaa ttccacaaac agaatgtttt caaggggcta tacagtttgc    1260
caggtctgaa gggttgatac cagctcctga accaactcat gccatagctg caaccattag    1320
ggaagctatt cgttgtagag aggctggaga ggccaaggtt attctgacag caatgtgtgg    1380
acatggccat tttgatctgc cagcttatga aaagtacttg caaggtaaca tggttgacct    1440
ctcattctca gaagacaaga tgaaagcttc actggccaat attcctcaag tgattacctg    1500
agttgaggct cattctattg tagtacagtg aggaacaagg aagacataat agtactttac    1560
ttgggaccaa aatgtatggt tctctgaaca catatatgta tctgagtttg ttttaggcaa    1620
catttgatcc atgccaagga aggtgcaact agtagttttt atgaattttt tttctttcaa    1680
gattgatgtg aaaatataga gtcttgcatt ttcaacgtgt gtccaacaca cttagagcat    1740
gtttgtttcc ttgttctaac tgcagtgcac gaattccaat gagtaaaacg aaaaagtaac    1800
caagttaann nnanaaa                                                   1817
```

<210> SEQ ID NO 4

-continued

<211> LENGTH: 499
<212> TYPE: PRT
<213> ORGANISM: Glycine max

<400> SEQUENCE: 4

```
His Glu Val Phe Pro Val Asn Ala Leu Pro Thr Pro Ser Pro Cys Phe
  1               5                  10                  15

His Ser Lys Val Gly Lys Gln Trp Pro Gln Gly Phe Ala Leu Ser Val
             20                  25                  30

Arg Pro Thr Asn Pro Lys Arg Leu Ser Ser Ala Cys Lys Val Arg Ala
         35                  40                  45

Thr Leu Gly Ala Ser Asp Lys Ser Ile Gly Ile Pro Asn Gln Trp Tyr
     50                  55                  60

Asn Val Ile Ala Asp Leu Pro Val Lys Pro Pro Pro Leu His Pro
 65                  70                  75                  80

Lys Thr Tyr Glu Pro Ile Lys Pro Asp Asp Leu Ser Pro Leu Phe Pro
                 85                  90                  95

Asp Glu Leu Ile Arg Gln Glu Ile Ala Ser Asp Arg Phe Ile Asp Ile
            100                 105                 110

Pro Asp Glu Val Leu Asp Val Tyr Lys Leu Trp Arg Pro Thr Pro Leu
        115                 120                 125

Ile Arg Ala Lys Arg Leu Glu Lys Leu Leu Asp Thr Pro Ala Arg Ile
130                 135                 140

Tyr Tyr Lys Tyr Glu Gly Val Ser Pro Ala Gly Ser His Lys Pro Asn
145                 150                 155                 160

Ser Ala Val Pro Gln Ala Trp Tyr Asn Leu Gln Ala Gly Val Lys Asn
                165                 170                 175

Val Val Thr Glu Thr Gly Ala Gly Gln Trp Gly Ser Ala Leu Ala Phe
            180                 185                 190

Ala Cys Ser Ile Phe Gly Leu Gly Cys Glu Val Trp Gln Val Arg Ala
        195                 200                 205

Ser Tyr Asp Ser Lys Pro Tyr Arg Arg Leu Met Met Gln Thr Trp Gly
    210                 215                 220

Ala Lys Val His Pro Ser Pro Ser Met Ile Thr Glu Ala Gly Arg Arg
225                 230                 235                 240

Met Leu Gln Glu Asp Pro Ser Pro Gly Ser Leu Gly Ile Ala Ile
                245                 250                 255

Ser Glu Ala Val Glu Val Ala Ala Lys Asn Ala Asp Thr Lys Tyr Cys
            260                 265                 270

Leu Gly Ser Val Leu Asn His Val Leu His Gln Ser Val Ile Gly
        275                 280                 285

Glu Glu Cys Ile Lys Gln Met Glu Ala Ile Gly Glu Thr Pro Asp Val
    290                 295                 300

Ile Ile Gly Cys Thr Gly Gly Gly Ser Asn Phe Ala Gly Leu Ser Phe
305                 310                 315                 320

Pro Phe Leu Arg Glu Lys Leu Asn Lys Lys Ile Asn Pro Val Ile Arg
                325                 330                 335

Ala Val Glu Pro Ala Ala Cys Pro Ser Leu Thr Lys Gly Val Tyr Thr
            340                 345                 350

Tyr Asp Tyr Gly Asp Thr Ala Gly Met Thr Pro Leu Met Lys Met His
        355                 360                 365

Thr Leu Gly His Asp Phe Val Pro Asp Pro Ile His Ala Gly Gly Leu
    370                 375                 380

Arg Tyr His Gly Met Ala Pro Leu Ile Ser His Val Phe Asp Leu Gly
```

|     |     |     |     |     |     |     |     |     |     |     |     |     |     |     |
| --- | --- | --- | --- | --- | --- | --- | --- | --- | --- | --- | --- | --- | --- | --- |
| 385 |     |     |     |     | 390 |     |     |     |     | 395 |     |     |     | 400 |

Leu Met Glu Ala Ile Ala Ile Pro Gln Thr Glu Cys Phe Gln Gly Ala
                              405                            410                            415

Ile Gln Phe Ala Arg Ser Glu Gly Leu Ile Pro Ala Pro Glu Pro Thr
                              420                            425                            430

His Ala Ile Ala Ala Thr Ile Arg Glu Ala Ile Arg Cys Arg Glu Ala
                              435                            440                            445

Gly Glu Ala Lys Val Ile Leu Thr Ala Met Cys Gly His Gly His Phe
    450                            455                            460

Asp Leu Pro Ala Tyr Glu Lys Tyr Leu Gln Gly Asn Met Val Asp Leu
465                              470                            475                            480

Ser Phe Ser Glu Asp Lys Met Lys Ala Ser Leu Ala Asn Ile Pro Gln
                              485                            490                            495

Val Ile Thr

<210> SEQ ID NO 5
<211> LENGTH: 543
<212> TYPE: DNA
<213> ORGANISM: Triticum aestivum
<220> FEATURE:
<221> NAME/KEY: unsure
<222> LOCATION: (377)
<221> NAME/KEY: unsure
<222> LOCATION: (480)
<221> NAME/KEY: unsure
<222> LOCATION: (482)
<221> NAME/KEY: unsure
<222> LOCATION: (534)

<400> SEQUENCE: 5

| | | | | | |
|---|---|---|---|---|---|
| ggttgactac | ccactgagca | gagcagcttt | cggggcgcga | tccaggaagc | caggaacggc | 60 |
| aaagcaggcg | gcgcggcggc | ggctccatcg | tgacgacaag | aaatggccac | cgccctccgc | 120 |
| cctccccggc | tcccagcagt | tccagagcaa | gcctcttcac | ttcatcgcct | accaaagtac | 180 |
| agagttgccg | tcactgggcg | taggagcttc | gccgccaggg | ccggctcgta | tccaggcaac | 240 |
| gtgggcgtcc | cgaagcaatg | gtacaacctc | atcgccgacc | tgccggtgaa | gccgccgccg | 300 |
| atgctgcacc | cggggaccac | cagccgctga | accccagcga | cctggcccct | ctcttccccg | 360 |
| acgagctcat | caagcangac | tcacggagga | gcgcttcatc | gacatacccg | acaagtccgg | 420 |
| gatgtctaca | actctggcgc | ccgacccact | gatcaagggc | aagaggctgg | agaactgtcn | 480 |
| gnacccggga | agtctactac | aagtacgagg | gactaacccg | cgggtccaca | aggnaacacg | 540 |
| cct | | | | | | 543 |

<210> SEQ ID NO 6
<211> LENGTH: 147
<212> TYPE: PRT
<213> ORGANISM: Triticum aestivum
<220> FEATURE:
<221> NAME/KEY: UNSURE
<222> LOCATION: (73)
<221> NAME/KEY: UNSURE
<222> LOCATION: (92)
<221> NAME/KEY: UNSURE
<222> LOCATION: (95)
<221> NAME/KEY: UNSURE
<222> LOCATION: (145)

<400> SEQUENCE: 6

Met Ala Thr Ala Leu Arg Pro Pro Arg Leu Pro Ala Val Pro Glu Gln
1                   5                           10                           15

-continued

```
Ala Ser Ser Leu His Arg Leu Pro Lys Tyr Arg Val Ala Val Thr Gly
             20                  25                  30

Arg Arg Ser Phe Ala Ala Arg Ala Gly Ser Tyr Pro Gly Asn Val Gly
         35                  40                  45

Val Pro Lys Gln Trp Tyr Asn Leu Ile Ala Asp Leu Pro Val Lys Pro
     50                  55                  60

Pro Pro Met Leu His Pro Gly Thr Xaa Gln Pro Leu Asn Pro Ser Asp
 65                  70                  75                  80

Leu Ala Pro Leu Phe Pro Asp Glu Leu Ile Lys Xaa Asp Ser Xaa Glu
                 85                  90                  95

Glu Arg Phe Ile Asp Ile Pro Asp Lys Ser Gly Met Ser Thr Thr Leu
            100                 105                 110

Ala Pro Asp Pro Leu Ile Lys Gly Lys Arg Leu Glu Asn Cys Arg Thr
        115                 120                 125

Arg Glu Val Tyr Tyr Lys Tyr Glu Gly Leu Thr Arg Gly Ser Thr Arg
    130                 135                 140

Xaa His Ala
145

<210> SEQ ID NO 7
<211> LENGTH: 434
<212> TYPE: PRT
<213> ORGANISM: Aquifex aeolicus

<400> SEQUENCE: 7

Met Arg Lys Phe Leu Leu Ser Glu Gly Glu Ile Pro Lys Lys Trp Leu
  1               5                  10                  15

Asn Ile Leu Pro Leu Leu Pro Glu Pro Leu Glu Pro Pro Leu Asp Pro
             20                  25                  30

Glu Thr Met Glu Pro Val Lys Pro Glu Lys Leu Leu Ala Ile Phe Pro
         35                  40                  45

Glu Pro Leu Val Glu Gln Glu Val Ser Asp Lys Glu Trp Ile Asp Ile
     50                  55                  60

Pro Glu Glu Val Leu Asp Ile Tyr Ser Leu Trp Arg Pro Thr Pro Leu
 65                  70                  75                  80

His Arg Ala Lys Asn Leu Glu Glu Phe Leu Gly Thr Pro Ala Lys Ile
                 85                  90                  95

Phe Tyr Lys Asn Glu Ser Val Ser Pro Pro Gly Ser His Lys Pro Asn
            100                 105                 110

Thr Ala Val Ala Gln Ala Tyr Tyr Asn Lys Ile Ser Gly Val Lys Arg
        115                 120                 125

Leu Thr Thr Glu Thr Gly Ala Gly Gln Trp Gly Ser Ala Leu Ser Phe
    130                 135                 140

Ala Thr Gln Phe Phe Asp Leu Gln Cys Arg Val Tyr Met Val Arg Val
145                 150                 155                 160

Ser Tyr Asn Gln Lys Pro Tyr Arg Arg Ile Leu Met Glu Thr Trp Lys
                165                 170                 175

Gly Glu Val Ile Pro Ser Pro Ser Pro Tyr Thr Asn Ala Gly Arg Lys
            180                 185                 190

Tyr Tyr Glu Glu Asn Pro Glu His Pro Gly Ser Leu Gly Ile Ala Ile
        195                 200                 205

Ser Glu Ala Ile Glu Glu Ala Ala Ser Arg Glu Asp Thr Lys Tyr Ser
    210                 215                 220

Leu Gly Ser Val Leu Asn His Val Leu Leu His Gln Thr Val Ile Gly
225                 230                 235                 240
```

```
Leu Glu Ala Lys Lys Gln Met Glu Glu Ala Gly Tyr Tyr Pro Asp Val
                245                 250                 255

Ile Ile Gly Ala Val Gly Gly Ser Asn Phe Ala Gly Leu Ser Phe
        260                 265                 270

Pro Phe Leu Ala Asp Val Leu Arg Gly Asp Lys Arg Lys Glu Asp Leu
        275                 280                 285

Lys Val Leu Ala Val Glu Pro Glu Ala Cys Pro Thr Leu Thr Lys Gly
        290                 295                 300

Glu Tyr Lys Tyr Asp Phe Gly Asp Ser Val Gly Leu Thr Pro Leu Ile
305                 310                 315                 320

Lys Met Tyr Thr Leu Gly His Asp Phe Val Pro Ser Pro Ile His Ala
                325                 330                 335

Gly Gly Leu Arg Tyr His Gly Asp Ala Pro Leu Val Cys Lys Leu Tyr
                340                 345                 350

Asn Leu Gly Tyr Ile Asp Ala Val Ala Tyr Lys Gln Thr Glu Val Phe
                355                 360                 365

Glu Ala Ala Val Thr Phe Ala Arg Thr Glu Gly Ile Val Pro Ala Pro
370                 375                 380

Glu Ser Ala His Ala Ile Lys Ala Ala Ile Asp Glu Ala Leu Lys Cys
385                 390                 395                 400

Lys Glu Thr Gly Glu Glu Lys Val Ile Leu Phe Asn Leu Ser Gly His
                405                 410                 415

Gly Tyr Phe Asp Leu Ser Ala Tyr Asp Lys Tyr Leu His Gly Glu Leu
                420                 425                 430

Thr Asp

<210> SEQ ID NO 8
<211> LENGTH: 389
<212> TYPE: PRT
<213> ORGANISM: Zea mays

<400> SEQUENCE: 8

Gly Arg Phe Gly Gly Lys Tyr Val Pro Glu Thr Leu Met His Ala Leu
  1               5                  10                  15

Thr Glu Leu Glu Asn Ala Phe His Ala Leu Ala Thr Asp Asp Glu Phe
                 20                  25                  30

Gln Lys Glu Leu Asp Gly Ile Leu Lys Asp Tyr Val Gly Arg Glu Ser
             35                  40                  45

Pro Leu Tyr Phe Ala Glu Arg Leu Thr Glu His Tyr Lys Arg Ala Asp
     50                  55                  60

Gly Thr Gly Pro Leu Ile Tyr Leu Lys Arg Glu Asp Leu Asn His Arg
 65                  70                  75                  80

Gly Ala His Lys Ile Asn Asn Ala Val Ala Gln Ala Leu Leu Ala Lys
                 85                  90                  95

Arg Leu Gly Lys Gln Arg Ile Ile Ala Glu Thr Gly Ala Gly Gln His
                100                 105                 110

Gly Val Ala Thr Ala Thr Val Cys Ala Arg Phe Gly Leu Gln Cys Ile
            115                 120                 125

Ile Tyr Met Gly Ala Gln Asp Met Glu Arg Gln Ala Leu Asn Val Phe
    130                 135                 140

Arg Met Lys Leu Leu Gly Ala Glu Val Arg Ala Val His Ser Gly Thr
145                 150                 155                 160

Ala Thr Leu Lys Asp Ala Thr Ser Glu Ala Ile Arg Asp Trp Val Thr
                165                 170                 175
```

```
Asn Val Glu Thr Thr His Tyr Ile Leu Gly Ser Val Ala Gly Pro His
            180                 185                 190

Pro Tyr Pro Met Met Val Arg Glu Phe His Lys Val Ile Gly Lys Glu
        195                 200                 205

Thr Arg Arg Gln Ala Met His Lys Trp Gly Lys Pro Asp Val Leu
        210                 215                 220

Val Ala Cys Val Gly Gly Ser Asn Ala Met Gly Leu Phe His Glu
225                 230                 235                 240

Phe Val Glu Asp Gln Asp Val Arg Leu Ile Gly Val Glu Ala Ala Gly
                245                 250                 255

His Gly Val Asp Thr Asp Lys His Ala Ala Thr Leu Thr Lys Gly Gln
                260                 265                 270

Val Gly Val Leu His Gly Ser Met Ser Tyr Leu Leu Gln Asp Asp Asp
            275                 280                 285

Gly Gln Val Ile Glu Pro His Ser Ile Ser Ala Gly Leu Asp Tyr Pro
            290                 295                 300

Gly Val Gly Pro Glu His Ser Phe Leu Lys Asp Ile Gly Arg Ala Glu
305                 310                 315                 320

Tyr Asp Ser Val Thr Asp Gln Glu Ala Leu Asp Ala Phe Lys Arg Val
                325                 330                 335

Ser Arg Leu Glu Gly Ile Ile Pro Ala Leu Glu Thr Ser His Ala Leu
            340                 345                 350

Ala Tyr Leu Glu Lys Leu Cys Pro Thr Leu Pro Asp Gly Val Arg Val
            355                 360                 365

Val Leu Asn Cys Ser Gly Arg Gly Asp Lys Asp Val His Thr Ala Ser
370                 375                 380

Lys Tyr Leu Asp Val
385

<210> SEQ ID NO 9
<211> LENGTH: 443
<212> TYPE: PRT
<213> ORGANISM: Zea mays

<400> SEQUENCE: 9

Pro Gly Pro Pro Pro Ala Pro Glu Gly Arg Arg Arg Gly Arg
1               5                   10                  15

Gly Arg Asn Ala Ala Gly Gln Ala Val Ala Ala Glu Ala Ser Pro Ala
            20                  25                  30

Ala Val Glu Met Gly Asn Gly Ala Ala Ala Pro Gly Leu Gln Arg Pro
        35                  40                  45

Asp Ala Met Gly Arg Phe Gly Arg Phe Gly Lys Tyr Val Pro Glu
    50                  55                  60

Thr Leu Met His Ala Leu Thr Glu Leu Glu Ser Ala Phe His Ala Leu
65                  70                  75                  80

Ala Thr Asp Asp Glu Phe Gln Lys Glu Leu Asp Gly Ile Leu Lys Asp
                85                  90                  95

Tyr Val Gly Arg Glu Ser Pro Leu Tyr Phe Ala Glu Arg Leu Thr Glu
            100                 105                 110

His Tyr Lys Arg Ala Asp Gly Thr Gly Pro Leu Ile Tyr Leu Lys Arg
        115                 120                 125

Glu Asp Leu Asn His Thr Gly Ala His Lys Ile Asn Asn Ala Val Ala
    130                 135                 140

Gln Ala Leu Leu Ala Lys Arg Leu Gly Lys Gln Arg Ile Ile Ala Glu
```

```
                145                 150                 155                 160
Thr Gly Ala Gly Gln His Gly Val Ala Thr Ala Thr Val Cys Arg Arg
                165                 170                 175
Phe Gly Leu Gln Cys Ile Ile Tyr Met Gly Ala Gln Asp Met Glu Arg
                180                 185                 190
Gln Ala Leu Asn Val Phe Arg Met Arg Leu Leu Gly Ala Glu Val Arg
                195                 200                 205
Ala Val His Ser Gly Thr Ala Thr Leu Lys Asp Ala Thr Ser Glu Ala
                210                 215                 220
Ile Arg Asp Trp Val Thr Asn Val Glu Thr Thr His Tyr Ile Leu Gly
225                 230                 235                 240
Ser Val Ala Gly Pro His Pro Tyr Pro Met Met Val Arg Glu Phe His
                245                 250                 255
Lys Val Ile Gly Lys Glu Thr Arg Arg Gln Ala Met Asp Lys Trp Gly
                260                 265                 270
Gly Lys Pro Asp Val Leu Val Ala Cys Val Gly Gly Gly Ser Asn Ala
                275                 280                 285
Met Gly Leu Phe His Glu Phe Val Glu Asp Gln Asp Val Arg Leu Val
                290                 295                 300
Gly Leu Glu Ala Ala Gly His Gly Val Asp Thr Asp Lys His Ala Ala
305                 310                 315                 320
Thr Leu Thr Lys Gly Gln Val Gly Val Leu His Gly Ser Met Ser Tyr
                325                 330                 335
Leu Leu Gln Asp Asp Asp Gly Gln Val Ile Glu Pro His Ser Ile Ser
                340                 345                 350
Ala Gly Leu Asp Tyr Pro Gly Val Gly Pro Glu His Ser Phe Leu Lys
                355                 360                 365
Asp Ile Gly Arg Ala Glu Tyr Asp Ser Val Thr Asp Gln Glu Ala Leu
370                 375                 380
Asp Ala Phe Lys Arg Val Ser Arg Leu Glu Gly Ile Ile Pro Ala Leu
385                 390                 395                 400
Glu Thr Ser His Ala Leu Ala Tyr Leu Glu Lys Leu Cys Pro Thr Leu
                405                 410                 415
Ala Asp Gly Val Arg Val Val Asn Cys Ser Gly Arg Gly Asp Lys
                420                 425                 430
Asp Val His Thr Ala Ser Lys Tyr Leu Asp Val
                435                 440

<210> SEQ ID NO 10
<211> LENGTH: 666
<212> TYPE: DNA
<213> ORGANISM: Oryza sativa
<220> FEATURE:
<221> NAME/KEY: unsure
<222> LOCATION: (73)
<221> NAME/KEY: unsure
<222> LOCATION: (580)
<221> NAME/KEY: unsure
<222> LOCATION: (609)
<221> NAME/KEY: unsure
<222> LOCATION: (640)
<221> NAME/KEY: unsure
<222> LOCATION: (648)
<221> NAME/KEY: unsure
<222> LOCATION: (650)
<221> NAME/KEY: unsure
<222> LOCATION: (658)
<221> NAME/KEY: unsure
<222> LOCATION: (661)
```

<400> SEQUENCE: 10

```
gaagagcgca agccgggaga agcaccacca cctagataga acaataaaaa ttgctgcatc      60
cgtcagagct ggncactaca aaaaccagct gcatcacagg agagagcagg cagagaggca     120
gctctccagc tcgcgtttgg ggttgaccag ttactccggg cgaaccgacg gcaagccggc     180
gccggcggcg agggtcgtcg ggagcggaag agagggagaa agaatggcca ccaccgcctc     240
cgtccgacct cccctgctcc gacaagcagc aggttcagaa aaagcctcac tcctttgcaa     300
accaaagcag agagcttctg tcagaagaag aagcttcact gccagggcca gctcgaatcc     360
tgtgagcatc ccgaagcaat ggtacaacct cgtcgccgac ctgccggtga agccaccgcc     420
gccgctgcac ccgcagacgc accagccact gaaccctagt gacctgtccc ctctcttccc     480
cgacgagctg atcaggcagg aggtgaccga ggagcggttc atcgacatcc cggaggaggt     540
cgccgaggtt tacaagctct ggcgcccgac gccgctgatn aaggcgaggg aggctggaga     600
agctgctgng cacgccggcg aatatttact acaaagtacn aagggganccn agcccggngg     660
nggtcc                                                                666
```

<210> SEQ ID NO 11
<211> LENGTH: 144
<212> TYPE: PRT
<213> ORGANISM: Oryza sativa
<220> FEATURE:
<221> NAME/KEY: UNSURE
<222> LOCATION: (119)
<221> NAME/KEY: UNSURE
<222> LOCATION: (129)
<221> NAME/KEY: UNSURE
<222> LOCATION: (139)
<221> NAME/KEY: UNSURE
<222> LOCATION: (142)

<400> SEQUENCE: 11

```
Met Ala Thr Thr Ala Ser Val Arg Pro Pro Leu Leu Arg Gln Ala Ala
  1               5                  10                  15

Gly Ser Glu Lys Ala Ser Leu Leu Cys Lys Pro Lys Gln Arg Ala Ser
             20                  25                  30

Val Arg Arg Arg Ser Phe Thr Ala Arg Ala Ser Ser Asn Pro Val Ser
         35                  40                  45

Ile Pro Lys Gln Trp Tyr Asn Leu Val Ala Asp Leu Pro Val Lys Pro
     50                  55                  60

Pro Pro Pro Leu His Pro Gln Thr His Gln Pro Leu Asn Pro Ser Asp
 65                  70                  75                  80

Leu Ser Pro Leu Phe Pro Asp Glu Leu Ile Arg Gln Glu Val Thr Glu
                 85                  90                  95

Glu Arg Phe Ile Asp Ile Pro Glu Glu Val Ala Glu Val Tyr Lys Leu
            100                 105                 110

Trp Arg Pro Thr Pro Leu Xaa Arg Arg Gly Arg Leu Glu Lys Leu Leu
        115                 120                 125

Xaa Thr Pro Ala Asn Ile Tyr Tyr Lys Val Xaa Arg Gly Xaa Ser Pro
    130                 135                 140
```

<210> SEQ ID NO 12
<211> LENGTH: 1709
<212> TYPE: DNA
<213> ORGANISM: Triticum aestivum

<400> SEQUENCE: 12

```
gcacgagggt tgactaccca ctgagcagag cagctttcgg ggcgcgatcc aggaagccag      60
```

-continued

```
gaacggcaaa gcaggcggcg cggcggcggc tccatcgtga cgacaagaaa tggccaccgc      120
cctccgccct ccccggctcc cagcagttcc agagcaagcc tcttcacttc atcgcctacc      180
aaagtacaga gttgccgtca ctgggcgtag gagcttcgcc gccagggccg gctcgtatcc      240
aggcaacgtg ggcgtcccga agcaatggta caacctcatc gccgacctgc cggtgaagcc      300
gccgccgatg ctgcacccgg gacgcacca gccgctgaac cccagcgacc tggcccctct      360
cttccccgac gagctcatca ggcaggagct cacggaggag cgcttcatcg acatacccga      420
cgaggtccgg gatgtctacg agctctggcg cccgacgcca ctgatcaggg ccaagaggct      480
ggagaagctg ctcggcacgc cggcgaagat ctactacaag tacgagggca ctagcccggc      540
ggggtcgcac aagggcaaca ccgccgtgcc gcaggcgtgg tacaacgccg cggcgggggt      600
caagaacgtg gtcaccgaga ccggcgccgg ccagtggggc agcgcgctct ccttcgccag      660
caccctcttc ggcctcaact gcgaggtgtg gcaggtgcgc gcgtcctacg accagaagcc      720
gtaccggagg ctgatgatgg agacgtgggg cgccaaggtg cacccgtcgc cgtccgacgt      780
gacggaggcc ggcaggaagc tcctggcgg ggacccggcc agcccgggga gcctcgggat      840
ggccatctcc gaggcggtgg aggtcgcggc caccaacgcc gacaccaagt actgcctcgg      900
cagcgtgctc aaccacgtcc tgctgcacca gaccgtcatc ggcgaggagt gcctggagca      960
gctggcggcc atcggcgaca ccccggacgt cgtcatcggc tgcaccggcg gcggctccaa     1020
cttcggcggg ctcgccttcc ccttcatgcg cgagaagctg gccggcagga tgagcccgca     1080
gttcaaggcc gtggagcccg cggcgtgccc cacgctcacc aagggcgtct acgcctacga     1140
ctacggcgac acgccgggc tgacgccgct catgaagatg cacaccctcg ccacgacatt      1200
tgtccccgat cccatccatg caggtgggct tcgctaccat ggaatggcgc tctctgatttc     1260 ccatgtgtat gagctcgggt tcatggaggc catgtccata cagcaaactg agtgcttcga     1320
agctgcattg caatttgcac ggacggaggg catcatccca gcgccggagc cgacgcacgc     1380
gatcgcggcg gcgatcaggg aagcgctgga gtgcaagagg accggggagg agaaggtcat     1440
cctcatcgcc atgtgcggcc acggccactt cgacctcgcc gcctacgacc ggtacctgag     1500
aggcgacatg attgatctct cgcactcctc cgagaagctc aaggagtctc tgggtgccat     1560
tcccaaagtc tgatgctaga gattcagaga ttgatagaag aacggtttgg gaagtgggaa     1620
tacaataaga tgaacaatgt gacgctttct tggtgcatgg cacacataaa tttgatcaat     1680
aaaagatgtt accttttggc taaaaaaaa                                        1709
```

<210> SEQ ID NO 13
<211> LENGTH: 487
<212> TYPE: PRT
<213> ORGANISM: Triticum aestivum

<400> SEQUENCE: 13

```
Met Ala Thr Ala Leu Arg Pro Pro Arg Leu Pro Ala Val Pro Glu Gln
  1               5                  10                  15

Ala Ser Ser Leu His Arg Leu Pro Lys Tyr Arg Val Ala Val Thr Gly
             20                  25                  30

Arg Arg Ser Phe Ala Ala Arg Ala Gly Ser Tyr Pro Gly Asn Val Gly
         35                  40                  45

Val Pro Lys Gln Trp Tyr Asn Leu Ile Ala Asp Leu Pro Val Lys Pro
     50                  55                  60

Pro Pro Met Leu His Pro Gly Thr His Gln Pro Leu Asn Pro Ser Asp
 65                  70                  75                  80
```

-continued

```
Leu Ala Pro Leu Phe Pro Asp Glu Leu Ile Arg Gln Glu Leu Thr Glu
                 85                  90                  95

Glu Arg Phe Ile Asp Ile Pro Asp Glu Val Arg Asp Val Tyr Glu Leu
            100                 105                 110

Trp Arg Pro Thr Pro Leu Ile Arg Ala Lys Arg Leu Glu Lys Leu Leu
            115                 120                 125

Gly Thr Pro Ala Lys Ile Tyr Tyr Lys Tyr Glu Gly Thr Ser Pro Ala
            130                 135                 140

Gly Ser His Lys Gly Asn Thr Ala Val Pro Gln Ala Trp Tyr Asn Ala
145                 150                 155                 160

Ala Ala Gly Val Lys Asn Val Val Thr Glu Thr Gly Ala Gly Gln Trp
                165                 170                 175

Gly Ser Ala Leu Ser Phe Ala Ser Thr Leu Phe Gly Leu Asn Cys Glu
            180                 185                 190

Val Trp Gln Val Arg Ala Ser Tyr Asp Gln Lys Pro Tyr Arg Arg Leu
            195                 200                 205

Met Met Glu Thr Trp Gly Ala Lys Val His Pro Ser Pro Ser Asp Val
        210                 215                 220

Thr Glu Ala Gly Arg Lys Leu Leu Ala Ala Asp Pro Ala Ser Pro Gly
225                 230                 235                 240

Ser Leu Gly Met Ala Ile Ser Glu Ala Val Glu Val Ala Ala Thr Asn
                245                 250                 255

Ala Asp Thr Lys Tyr Cys Leu Gly Ser Val Leu Asn His Val Leu Leu
            260                 265                 270

His Gln Thr Val Ile Gly Glu Glu Cys Leu Glu Gln Leu Ala Ala Ile
            275                 280                 285

Gly Asp Thr Pro Asp Val Val Ile Gly Cys Thr Gly Gly Gly Ser Asn
290                 295                 300

Phe Gly Gly Leu Ala Phe Pro Phe Met Arg Glu Lys Leu Ala Gly Arg
305                 310                 315                 320

Met Ser Pro Gln Phe Lys Ala Val Glu Pro Ala Ala Cys Pro Thr Leu
            325                 330                 335

Thr Lys Gly Val Tyr Ala Tyr Asp Tyr Gly Asp Thr Ala Gly Leu Thr
            340                 345                 350

Pro Leu Met Lys Met His Thr Leu Gly His Asp Phe Val Pro Asp Pro
            355                 360                 365

Ile His Ala Gly Gly Leu Arg Tyr His Gly Met Ala Pro Leu Ile Ser
            370                 375                 380

His Val Tyr Glu Leu Gly Phe Met Glu Ala Met Ser Ile Gln Gln Thr
385                 390                 395                 400

Glu Cys Phe Glu Ala Ala Leu Gln Phe Ala Arg Thr Glu Gly Ile Ile
            405                 410                 415

Pro Ala Pro Glu Pro Thr His Ala Ile Ala Ala Ala Ile Arg Glu Ala
            420                 425                 430

Leu Glu Cys Lys Arg Thr Gly Glu Glu Lys Val Ile Leu Ile Ala Met
            435                 440                 445

Cys Gly His Gly His Phe Asp Leu Ala Ala Tyr Asp Arg Tyr Leu Arg
        450                 455                 460

Gly Asp Met Ile Asp Leu Ser His Ser Ser Glu Lys Leu Lys Glu Ser
465                 470                 475                 480

Leu Gly Ala Ile Pro Lys Val
                485
```